United States Patent [19]

Peet et al.

[11] Patent Number: 5,478,811
[45] Date of Patent: Dec. 26, 1995

[54] ORALLY-ACTIVE ELASTASE INHIBITORS

[75] Inventors: Norton P. Peet; Michael R. Angelastro, both of Cincinnati; Joseph P. Burkhart, West Chester, all of Ohio

[73] Assignee: Merrell Dow Pharmaceuticals Inc., Cincinnati, Ohio

[21] Appl. No.: 323,418

[22] Filed: Oct. 13, 1994

Related U.S. Application Data

[63] Continuation of Ser. No. 127,966, Sep. 28, 1993, abandoned, which is a continuation of Ser. No. 918,561, Jul. 29, 1992, abandoned, which is a continuation-in-part of Ser. No. 748,607, Aug. 22, 1991, abandoned.

[51] Int. Cl.$^6$ ............................. A61K 38/00; C07K 5/00; C07K 7/00; C07K 17/00
[52] U.S. Cl. ............................. 514/17; 514/18; 530/330; 530/331
[58] Field of Search ..................... 514/17–18; 530/330, 530/331

[56] References Cited

U.S. PATENT DOCUMENTS

| | | | |
|---|---|---|---|
| 4,277,395 | 7/1981 | Bey et al. | |
| 4,518,528 | 5/1985 | Rasnick | 514/17 |
| 4,623,639 | 11/1986 | Hassall | 514/18 |
| 4,629,724 | 12/1986 | Ryono et al. | 514/18 |
| 4,636,489 | 1/1987 | Seemuller et al. | 514/12 |
| 4,643,991 | 2/1987 | Digenis | 514/18 |
| 4,855,303 | 8/1989 | Hoover | |
| 4,873,221 | 10/1989 | Trainor | 514/18 |
| 4,880,780 | 11/1989 | Trainor et al. | 514/18 |
| 4,910,190 | 3/1990 | Bergeson et al. | 514/19 |
| 4,935,405 | 6/1990 | Hoover et al. | 514/19 |
| 5,055,450 | 10/1991 | Edwards et al. | 514/19 |
| 5,114,927 | 5/1992 | Schirlin | 514/18 |
| 5,162,307 | 11/1992 | Digenis et al. | 514/19 |

FOREIGN PATENT DOCUMENTS

| | | |
|---|---|---|
| 0318318 | 11/1988 | European Pat. Off. |
| 0369391 | 5/1990 | European Pat. Off. |
| 0410411 | 1/1991 | European Pat. Off. |
| 0494071 | 8/1992 | European Pat. Off. |
| 9115487 | 3/1990 | WIPO |
| 9113904 | 3/1991 | WIPO |
| 9215605 | 9/1992 | WIPO |

OTHER PUBLICATIONS

*Biochemistry*, Imperiali et al., Inhibition of Serene Protease by Peptidyl Flourumethyl Ketones, vol. 25, pp. 3760–3767 (1986).

Shah et al, "Orally Active β–Lactam Inhibitors of Human Leukocyte Elastase-1". *J. Med Chem*, 35, pp. 3745–3754 (1992).

Snider, "Experimental Studies on Emphysema and Chronic Bronchial Injury", *Eur. J. Respir Dis* (1986) 69 (Suppl. 146) pp. 17–35.

Malech et al, "Current Concepts: Immunology Neutrophils in Human Diseases", *New Engl. J. Med.*, 317, 687–694 (1987).

Fletcher et al, "A comparison of $\alpha_1$_ Proteinase Inhibitor Methoxysuccinyl–ala–ala–pro–val–chloromethylketone and Specific β–Lactam Inhibitors in a accute Model of Human Polymorphonuclear Leukocyte Elastase–induced Lung Hemorrhage in the hamster", *Am Rev Respir* (1990); 141:672–677.

Hassall et al, "A new class of inhibitors of human leucocyte elastase", *FEBS Lett.*, 183, 201–205 (1985).

Travis, J. et al., "Potential Problems in Designing Elastase Inhibitors for Therapy," Am Rev Respir Dis, Pulmonary Perspective, vol. 143 pp. 1412–1415 1991.

Petrillo, E. W., et al., Chapter 6. Antihypertensive Agents, Section II. Cardiovascular and Pulmonary Agents, Annual Reports in Medicinal Chemistry, 25, 1989, Academic Press, Inc., D. W. Robertson Editor.

Chemical Abstract vol. 111, No. 21, Nov. 20, 1989, Galzigna et al. Abst #190131z.

Chemical Abstract Vo. 111, No. 9, Aug. 28, 1989, Lafuma et al Abst. #70314q.

Peet et al., "Synthesis of Peptidyl Fluoromethyl Ketones and Peptidyl α–Keto Esters as Inhibitors of Porcine Pancreativ Elastase, Human Neutrophil Elastase, and Rat and Human Neutrophil Cathepsin G", *J. Med. Chem.* 33, pp. 394–407, (1990).

Angelastro, et al., "Inhibition of Human Neutrophil Elastase with Peptidyl Electrophilic Ketones. 2. Orally Active $P_G$–Val–Pro–Val Pentafluoroethyl Ketones" *J. Med. Chem. 37*, pp. 4538–4553, (1994).

"Communications tothe Editor", *J. Med. Chem. 33*, pp. 11–13, (1990).

Angelastro et al., "Synthesis of a Peptidyl 2,2–Difluror–3–Aminopropionate", *Biorganic and Medicinal Chemistry Letters, vol. 2*, pp. 1235–1238, (1992).

Angelastro, et al., "Janus Compounds: Dual Inhibitors of Proteinases", *Bioorganic and Medicinal Chemistry Letters, vol. 3*, No. 4, pp. 525–530, (1993).

Mehdi, S., "Synthetic and Naturally Occurring Protease Inhibitors Containing an Electrophilic Carbonyl Group", *Bioorganic Chemistry 21*, pp. 249–259, (1993).

Angelastro, et al., "Efficient Preparation of Peptidyl Pentafluoroethyl Ketones", *Tetrahedron Letters*, vol. 33, No. 23, pp. 3265–3268, (1992).

Burkhart, et al., "A Novel Method for the Preparation of Peptidyl α–Keto Esters" *Tetrahedron Letters*, vol. 33, No. 23, pp. 3265–3268, (1992).

Angelastro, et al, "An Efficient Synthesis of Novel α–Diketone and α–Keto Ester Derivatives of N–Protected Amino Acids and Peptides" *J. Org. Chem.* 54, pp. 3913–3916, (1989).

Burkhart et al., "Inhibition of Human Neutrophil Elastase. 3. An Orally Active Enol Acetate Prodrug" *J. Med. Chem.* 38, (1995) p. 223.

(List continued on next page.)

Primary Examiner—Jill Warden
Assistant Examiner—Sheela J. Huff
Attorney, Agent, or Firm—William R. Boudreaux

[57] ABSTRACT

This invention relates to novel morpholinourea and related derivatives of pentafluoroethyl peptides which are orally active elastase inhibitors. These compounds are useful in the treatment of various inflammatory diseases and emphysema.

8 Claims, No Drawings

OTHER PUBLICATIONS

Skiles et al., *J. of Medicinal Chemistry*, vol. 35, No. 4, pp. 641–662 (1992).

Repine et al., *J. Med. Chem. 34*, pp. 1935–1943, (1991).

Ueda et al., *Biochem. J. 265*, pp. 539–545, (1990).

Sham, H. L. et al., *FEBS Letters*, Vo. 1. 220, No. 2, pp. 299–301, (1987).

Powers, J. C., *Eleventh American Peptide Syposium*, Abstracts, The Salk Institute and U. of CA, San Diego (1989).

Mehdi, et al, Biochemical and Biophysical Research Communications, pp. 595–600, vol. 166, No. 2, 1990.

Doherty et al, Int. J. Immunopharmac. Vo. 12, No. 7, pp. 787–795, 1990.

Peet, et al., 1989 American Chemical Society, J. Med. Chem, 1990, 33, 394–407.

Travis et al, Structure, Functino and Control of Neutrophil Proteinases, Jun. 24, 1988, The American Journal of Medicine, vol. 84, pp. 37–42.

Rice et al., Science, vol. 249, pp. 178–181 (1990).

Nakajima et al., The Journal of Biological Chemistry, vol. 254, No. 10, pp. 4027–4032 (1979).

Reilly et al., Biochimica et Biophysica Acta, vol. 621, pp. 147–157 (1980).

McWherter et al., Biochemistry, vol. 28, No. 14, pp. 5708–5714 (1989).

Steinmeyer et al., Arneimittel–Forschung/Drug Research, vol. 41(1), o.1, pp. 77–80 (1991).

Powers et al., Chemical Abstracts 108: 33954r (1988).

SEQUENCE LISTING ( 1 ) GENERAL INFORMATION:

```
( i i i ) NUMBER OF SEQUENCES: 5

( 2 ) INFORMATION FOR SEQ ID NO:1:

( i ) SEQUENCE CHARACTERISTICS:
                ( A ) LENGTH: 4 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:1:

Xaa  Xaa  Xaa  Xaa
        1

( 2 ) INFORMATION FOR SEQ ID NO:2:

( i ) SEQUENCE CHARACTERISTICS:
                ( A ) LENGTH: 4 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note="morpholino carbonyl
                        protected"

( i x ) FEATURE:
                ( A ) NAME/KEY: Modified-site
                ( B ) LOCATION: 4
                ( D ) OTHER INFORMATION: /note="terminal OH is replaced by
                        a perfluoroethyl group"

( x i ) SEQUENCE DESCRIPTION: SEQ ID NO:2:

Ala  Ala  Pro  Val
        1

( 2 ) INFORMATION FOR SEQ ID NO:3:

( i ) SEQUENCE CHARACTERISTICS:
                ( A ) LENGTH: 4 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note=
                        " 4(morpholinocarbonyl)benzoyl protected"

( i x ) FEATURE:
                ( A ) NAME/KEY: Modified-site
                ( B ) LOCATION: 4
                ( D ) OTHER INFORMATION: /note="terminal OH group replaced
                        by a perfluoroethyl group"

( x i ) SEQUENCE DESCRIPTION: SEQ ID NO:3:

Ala  Ala  Pro  Val
        1

( 2 ) INFORMATION FOR SEQ ID NO:4:

( i ) SEQUENCE CHARACTERISTICS:
                ( A ) LENGTH: 4 amino acids
                ( B ) TYPE: amino acid
                ( D ) TOPOLOGY: linear
```

(i i) MOLECULE TYPE: peptide (x i) SEQUENCE DESCRIPTION: SEQ ID NO:4:

Xaa Xaa Xaa Xaa
1

(2) INFORMATION FOR SEQ ID NO:5:

(i) SEQUENCE CHARACTERISTICS:
(A) LENGTH: 4 amino acids
(B) TYPE: amino acid
(D) TOPOLOGY: linear (i i) MOLECULE TYPE: peptide (x i) SEQUENCE DESCRIPTION: SEQ ID NO:5:

Xaa Xaa Xaa Xaa
1

ORALLY-ACTIVE ELASTASE INHIBITORS

CROSS-REFERENCE TO RELATED APPLICATION

This is a continuation of application Ser. No. 08/127,966, filed Sep. 28, 1993, now abandoned, which is a continuation of application Ser. No. 07/918,561 filed Jul. 29, 1992, now abandoned, which is a Continuation in Part of application Ser. No. 07/748,607 filed Aug. 22, 1991, now abandoned which is herein incorporated by reference.

This invention relates to orally-active elastase inhibitors useful for a variety of physiological end-use applications.

In its broad aspects, this invention relates to analogs of peptidase substrates in which the carboxy terminal carboxyl group has been replaced by a pentafluoroethylcarbonyl (—C(O)C$_2$F$_5$)group and in which the amino terminal amino acid is protected by various heterocycle-containing groups such as a 4-morpholinecarbonyl group. These elastase inhibitors exert valuable pharmacological activities and therefore have useful physiological consequences in a variety of disease states.

In its more specific aspects, this invention relates pentafluoroethylcarbonyl analogs of certain elastase substrates which have various heterocyclic containing protecting groups which are useful in inhibiting elastase, the inhibition of which will have useful physiological consequences in a variety of disease states.

The contemplated elastase inhibitors are selected from the generic formula

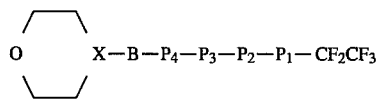

SEQ. ID 1 wherein

P$_1$ is Ala, bAla, Leu, Ile, Val, Nva, bVal, Met, Nle, Gly, or an N-methyl derivative;

P$_2$ is Ala, bAla, Leu, Ile, Val, Nva, bVal, Met, Nle, Gly, Phe, Tyr, Trp, or Nal(1) where the nitrogen of the alpha-amino group can be substituted with an R group where R is a (C$_{1-6}$)alkyl, (C$_{3-12}$)cycloalkyl, (C$_{3-12}$)cycloalkyl(C$_{1-6}$)alkyl, (C$_{4-11}$)bicycloalkyl, (C$_{4-11}$)bicycloalkyl(C$_{1-6}$)alkyl, (C$_{6-10}$)aryl, (C$_{6-10}$)aryl(C$_{1-6}$)alkyl, (C$_{3-7}$)heterocycloalkyl, (C$_{3-7}$)heterocycloalkyl(C$_{1-6}$)alkyl, (C$_{5-9}$)heteroaryl, (C$_{5-9}$)heteroaryl(C$_{1-6}$)alkyl, fused (C$_{6-10}$)aryl-(C$_{3-12}$)cycloalkyl, fused (C$_{6-10}$)aryl(C$_{3-12}$)cycloalkyl (C$_{1-6}$)alkyl, fused (C$_{5-9}$)heteroaryl(C$_{3-12}$)cycloalkyl, or fused (C$_{5-9}$)heteroaryl(C$_{3-12}$)cycloalkyl(C$_{1-6}$)alkyl, or P$_2$ is Pro, 1,2,3,4-tetrahydro-3-isoquinoline carboxylic acid (Tic), thiazolidine-4-acid (Tca), or Ind;

P$_3$ is Ala, bAla, Leu, Ile, Val, Nva, bVal, Met, or Nle or an N-methyl derivative, Pro, Ind, Tic or Tca, Lys or Orn each substituted on its omega amino group with a morpholino-B-group;

P$_4$ is Ala, bAla, Leu, Ile, Val, Nva, bVal, Met, or Nle or an N-methyl derivative or a bond; and B is a group of the formulae

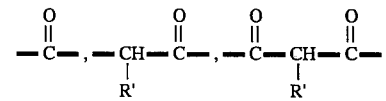

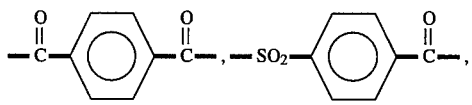

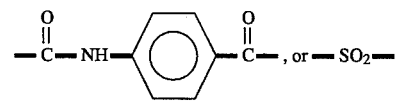

R' is a hydrogen or a C$_{1-6}$ branched or straight chain alkyl group;

X is N or CH; or a hydrate, isostere, or pharmaceutically acceptable salt thereof.

Isosteres of the compounds of formula 1 include those wherein (a) one or more of the α-amino residues of the P$_{1-P4}$ substituents are in its unnatural configuration (when there is a natural configuration) or (b) when the normal peptidic amide linkage is modified, such as for example, to form —CH$_2$NH— (reduced), —COCH$_2$— (keto), —CH(OH)CH$_2$— (hydroxy), —CH(NH$_2$)CH$_2$— (amino), —CH$_2$CH$_2$— (hydrocarbon), —CH=CH— (alkene). Preferably a compound of the invention should not be in an isosteric form; particularly it is preferred that there be no modified peptidic amide group, but if there is, it is preferable to keep the isosteric modifications to a minimum. Of course, it is also understood that in those instances wherein the carbonyl moiety of P$_1$ is in its reduced form, then such compounds are not hydrates.

As used herein the term "(C$_{1-6}$)alkyl" means a straight or branched alkyl group of from 1 to 6 carbon atoms, such as, methyl, ethyl, n-propyl, isopropyl, n-butyl, tert-butyl, n-pentyl, sec-pentyl, iso-pentyl, and n-hexyl. The term "(C$_{3-12}$)cycloalkyl" means a cyclic alkyl group consisting of a 3 to 8 member ring which can be substituted by a lower alkyl group, for example, cyclopropyl, cyclobutyl, cyclopentyl, cyclohexyl, 4-methylcyclohexyl, 4-ethylcyclohexyl, cycloheptyl, and cyclooctyl. The term "(C$_{3-12}$)cycloalkyl(C$_{1-6}$)alkyl" means a (C$_{1-6}$)alkyl group substituted by a (C$_{3-12}$)cycloalkyl group, such as a cyclohexylmethyl or cyclopentylethyl group. The term "(C$_{4-11}$)bicycloalkyl" means an alkyl group containing one pair of bridgehead carbon atoms, such as 2-bicyclo[1.1.0]-butyl, 2-bicyclo [2.2.1]hexyl, and 1-bicyclo[2.2.21]octane. The term "(C$_{4-11}$)bicycloalkyl(C$_{1-6}$)alkyl" means a (C$_{1-6}$)alkyl substituted by a (C$_{4-11}$)bicycloalkyl, such as 2-bicyclohexylmethyl. The term "(C$_{6-10}$)aryl" means a cyclic, aromatic assemblage of conjugated carbon atoms, for example, phenyl, 1-naphthyl, and 2-naphthyl. The term "(C$_{6-10}$)aryl(C$_{1-6}$)alkyl" means a (C$_{1-6}$)alkyl substituted by a (C$_{6-10}$)aryl, such as benzyl, phenethyl, and 1-naphthylmethyl. The term "(C$_{3-7}$)heterocycloalkyl" means a nonaromatic, carbon containing cyclic group which contains from 1 to 3 heteroatoms selected from oxygen, nitrogen and sulfur, such as morpholinyl and piperidinyl. The term "(C$_{3-7}$)heterocycloalkyl(C$_{1-6}$)alkyl" means a (C$_{1-6}$)alkyl group substituted by a (C$_{3-7}$)heterocycloalkyl group, for example, morpholinomethyl. The term "(C$_{5-9}$)heteroaryl" means a cyclic or bicyclic, aromatic assemblage of conjugated carbon atoms and from 1 to 3 nitrogen, oxygen, and sulfur atoms, for example, pyridinyl, 2-quinoxalinyl, and quinolinyl. The term "(C$_{5-9}$)heteroaryl($C_{1-6}$)alkyl" means ($C_{1-6}$)alkyl group substituted by a ($C_{5-9}$)heteroaryl group, such as, 3-quinolinylmethyl. The term "fused ($C_{6-10}$)aryl($C_{3-12}$)cycloalkyl" means a "($C_{3-12}$)cycloalkyl" group which has one or more sides shared with a "($C_{6-10}$)aryl" group and can, for example, include groups derived by the fusion of benzene and cyclopentane, that is 2-indanyl. The term "fused ($C_{6-10}$)aryl($C_{3-12}$)cycloalkyl($C_{1-6}$)alkyl" means a ($C_{1-6}$)alkyl substituted by a fused ($C_{6-10}$)aryl($C_{3-12}$)cycloalkyl group. The term "fused ($C_{5-9}$) heteroaryl($C_{3-8}$)cycloalkyl" means a ($C_{5-9}$)heteroaryl group which has one or more sides shared with a ($C_{3-8}$)cycloalkyl group and can, for example, include groups derived by the fusion of cyclohexane and pyridine, that is tetrahydroquinoline. Finally the term "fused ($C_{5-9}$)heteroaryl($C_{3-8}$)cycloalkyl($C_{1-6}$)alkyl" means a ($C_{1-6}$)alkyl substituted by a fused ($C_{5-9}$)heteroaryl($C_{3-8}$)cycloalkyl group.

Unless otherwise stated, the α-amino acids of these peptidase substrate analogs are preferably in their L-configuration; however, applicants contemplate that the amino acids of the formula 1 compounds can be of either the D- or L- configurations or can be mixtures of the D- and L-isomers, including the racemic mixture. Also, the carbon adjacent to the carboxy terminal —C(=O)CF$_2$CF$_3$ moiety can also be the D- or the L-optical isomer and can also be a mixture of such isomers. The recognized abbreviations for the a-amino acids are set forth in Table I.

TABLE I

| AMINO ACID | SYMBOL |
| --- | --- |
| Alanine | Ala |
| Glycine | Gly |
| Isoleucine | Ile |
| Leucine | Leu |
| Lysine | Lys |
| Phenylalanine | Phe |
| Proline | Pro |
| Tryptophan | Trp |
| Tyrosine | Tyr |
| Valine | Val |
| Norvaline | Nva |
| Norleucine | Nle |
| 1-Naphthylalanine | Nal (1) |
| 2-Indolinecarboxylic acid | Ind |
| Sarcosine | Sar |
| beta-Alanine | bAla |
| beta-Valine | bVal |
| Methionine | Met |
| 1,2,3,4-Tetrahydro-3-isoquinoline carboxylic acid | Tic |
| Thiazolidine-4-carboxylic acid | Tca |
| Ornithine | Orn |

Some of the preferred compounds of this invention are also morpholino urea derivatives by virtue of the fact that the amino terminal amino group of the peptide chain is protected by a 4-morpholinecarbonyl group. The 4-morpholinecarbonyl protecting group of the formula

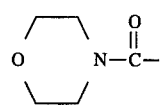

is abbreviated throughout as MC. Other preferred compounds of this invention are 4-morpholinecarbonylbenzoyl, abbreviated throughout as MCBz, derivatives wherein the morpholine-B group is of the formula

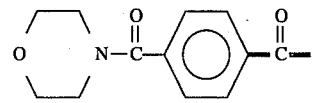

Yet other preferred compounds of this invention are 4-morpholine sulfonylbenzoyl derivatives wherein the morpholine-B group is of the formula

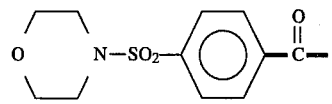

Still other preferred compounds of this invention are 2-(N-morpholinocarbonyl)-3-methyl-butanoyl derivatives wherein the morpholine-B group is of the formula

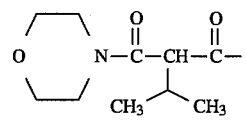

Of the compounds of formula 1 applicants also prefer those compounds wherein $P_1$ is norvaline or valine. Also preferred are those formula 1 compounds wherein $P_2$ is a proline or glycine; wherein $P_3$ is isoleucine, valine, or alanine; and wherein $P_4$ is alanine or is a bond. Other preferred compounds of formula 1 are those wherein alpha amino group of the $P_2$ group is substituted by an R group, especially those wherein the R group is a methyl group or a 2-indanyl group. Specifically preferred compounds of formula 1 are:

| | |
| --- | --- |
| MC—Ala—Ala—Pro—Val—C$_2$F$_5$, | SEQ. ID 2 |
| MC—Val—Pro—Val—C$_2$F$_5$, | |
| MCBZ—Ala—Ala—Pro—Val—C$_2$F$_5$, and | SEQ. ID 3 |
| MCBZ—Val—Pro—Val—C$_2$F$_5$. | |

Human leukocyte elastase is released by polymorphonuclear leukocytes at sites of inflammation and thus is a contributing cause for a number of disease states. Thus the peptidase substrates of formula 1 have an anti-inflammatory effect useful in the treatment of gout, rheumatoid arthritis and other inflammatory diseases, such as adult respiratory distress syndrome, septicemia, and disseminated intravascular coagulation, cystic fibrosis, and in the treatment of emphysema. In their end-use application the enzyme inhibitory properties of the compounds of formula 1 are readily ascertained by standard biochemical techniques well known in the art. Potential dose range for their end-use application will of course depend upon the nature and severity of the disease state as determined by the attending diagnostician with the range of 0.01 to 200 mg/kg body weight per day being useful for the aforementioned disease states with 0.1 mg to 50 mg/kg per day being preferred.

Human elastase is assayed in vitro using chromophoric peptides, succinylalanylalanylalanyl-p-nitroanilide, methoxysuccinylalanylalanylprolylvalyl-p-nitroanilide, and others, all of which are available commercially. The assay buffer, pH 8.0, and assay techniques are similar to those described by R. Lottenberg, et al., *Biochimica et Biophysica Acta*, 742, pp. 539–557 (1983). Enzyme is purified from human sputum, although recently it has become commercially available. Kinetic characterization of immediate inhibitors is by means of the Dixon plot, whereas the characterization of slow- and/or tight-binding inhibitors used data analysis techniques reviewed by Williams and Morrison. The synthesis and analytical use of a highly sensitive and convenient substrate of elastase is described in J. Bieth, B. Spiess and C. G. Wermuth, *Biochemical Medicine.*, 11 (1974) 350–375. Table 2 summarizes the ability of selected compounds of this invention and a compound of the prior art to inhibit elastase. Table 3 summarizes the oral activity of various compounds when evaluated in the elastase-induced hemmorrhage model in hamster.

TABLE 2

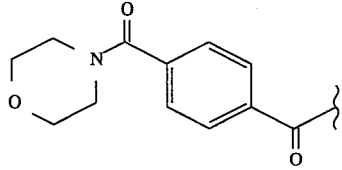

( R—ValProValC$_2$F$_5$ )

| MDL # | R | $K_i$(nM)* |
|---|---|---|
| 101,146 | 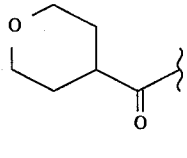 | 20 |
| 102,823 | 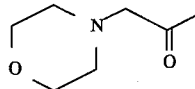 | 60 |
| 100,948A | 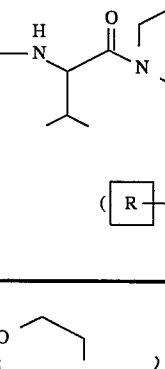 .HCl | 60 |

TABLE 2-continued

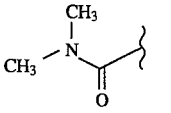

( R—ValProValC$_2$F$_5$ )

| MDL # | R | $K_i$(nM)* |
|---|---|---|
| 102,111 | 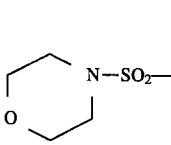 | 170 |
| 101,773 | 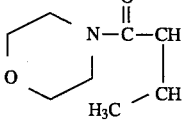 | 261 |
| 101,788 | 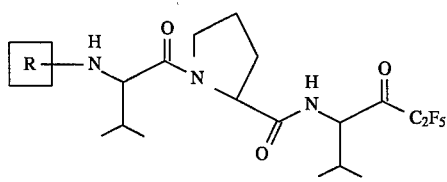 | 2.36 |
| 100,050 | 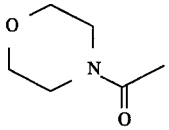 | 44 |

*for human neutrophil elastase, using N—MeOSucAlaAlaProVal-pNA as substrate

TABLE 3

SUMMARY OF ORALLY ACTIVE ELASTASE INHIBITORS

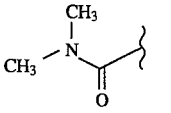

| MDL Number | R | $K_i$(nM) | Dose | % Inhibition |
|---|---|---|---|---|
| 102,111 | 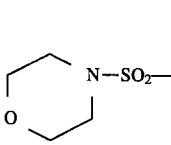 | 170 | 100 mg/Kg | 79* |
| | | | 50 mg/Kg | 70* |
| | | | 25 mg/Kg | 61* |
| | | | 10 mg/Kg | 30 |

TABLE 3-continued

SUMMARY OF ORALLY ACTIVE ELASTASE INHIBITORS

[Structure: R—NH—CH(iPr)—C(O)—N(pyrrolidine)—C(O)—NH—CH(iPr)—C(O)—$C_2F_5$]

| MDL Number | R | $K_i$(nM) | Dose | % Inhibition |
|---|---|---|---|---|
| 100,948A | morpholine-N-CH2-C(O)— .HCl | 60 | 50 mg/Kg | 77* |
|  |  |  | 10 mg/Kg | 39 |
| 101,230 | morpholine-N-C(O)-CH2-C(O)— | 70 | 25 mg/Kg | 41 |
|  |  |  | 10 mg/Kg | 0 |
| 101,146 | morpholine-N-C(O)-C6H4-C(O)CH3 | 20 | 50 mg/Kg | 74* |
|  |  |  | 25 mg/Kg | 56* |
|  |  |  | 10 mg/Kg | 25 |
| 100,867 | morpholine-N-C(O)-NH-C6H4-C(O)CH3 | 43 | 50 mg/Kg | 26 |
|  |  |  | 10 mg/Kg | 0 |

*means significant at P < .05

In general, the compounds of formula I may be prepared using standard chemical reactions analogously known in the art. The procedure for preparing the formula I compounds wherein B is —CO— is outlined in Scheme A wherein $P_1$, $P_2$, $P_3$, and $P_4$ are as previously defined or are functional equivalents of these groups and Pg is an amino protecting group such as a carbamate, preferably a t-butyloxycarbonyl (Boc) group. The compounds of Formula I wherein B is other than —CO— can be prepared analogously, merely by substituting the appropriate intermediate, which can be the corresponding acid or sulphonyl chloride or the acid for the compound of formula 6 in Scheme A.

SCHEME A $$Pg-P_4-P_3-P_2-OH \;+\; H-P_1-\overset{O}{\underset{\|}{C}}-CF_2CF_3$$
$$2 \qquad\qquad 3$$

↓ IBCF/NMM $$Pg-P_4-P_3-P_2-P_1-\overset{O}{\underset{\|}{C}}-CF_2CF_3 \qquad \text{SEQ. ID 4}$$
$$4$$

↓ Deprotection

-continued
SCHEME A

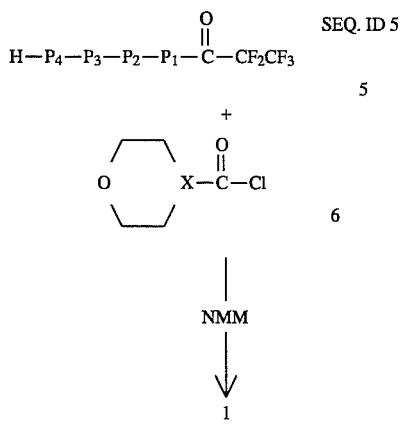

Specifically the compounds of this invention are prepared by coupling of the amino terminal amino unprotected pentafluoroethyl compounds of formula 5 with acid chloride, 6, in the presence of from one to four molar equivalents of a suitable amine which can act as a hydrogen halide acceptor. Suitable amines for use as hydrogen halide acceptors are tertiary organic amines such as tri-(lower alkyl)amines, for example, triethylamine, or aromatic amines such as picolines, collidines, and pyridine. When pyridines, picolines, or collidines are employed, they can be used in high excess and act therefore also as the reaction solvent. Particularly suitable for the reaction is N-methylmorpholine ("NMM"). The coupling reaction can be performed by adding an excess, such as from 1–5, preferably about a 4-fold molar excess of the amine and then the acid chloride, to a solution of the formula 5 pentafluoroethyl ketone. The solvent can be any suitable solvent, for example, petroleum ethers, a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethylether, tetrahydrofuran, or 1,4-dioxane, or an aromatic solvent such as benzene, toluene, or xylene. Methylene chloride is the preferred solvent for this coupling reaction. The reaction is allowed to proceed for from about 15 minutes to about 6 hours, depending on the reactants, the solvent, the concentrations, and other factors, such as the temperature which can be from about 0° C. to about 60° C., conveniently at about room temperature, i.e. 25° C. The formula 1 product can be isolated from the reaction mixture by any appropriate techniques such as by chromatography on silica gel eluting with, for example, a mixture of acetone and ethyl acetate.

The formula 5 pentafluoroethyl peptide can be prepared by, for example, protecting group removal from the corresponding formula 4 pentafluoroethyl peptide which is in turn prepared by the reaction of the formula 2 di- or tri-peptide and the pentafluoroethyl derivative of the $P_1$ amino acid, 3. The reaction of the formula 2 di- or tri-peptide with the formula 3 compound can be promoted by procedures known to promote peptide amide bond formation, such as by reacting the formula 2 di- or tri-peptide with isobutyl chloroformate ("IBCF") preferably in the presence of a HCl acceptor such as mentioned above, preferably NMM, and then adding the formula 3 compound. The reaction of the formula 2 peptide with IBCF is performed by, for example, adding about an equimolar amount of IBCF to a cooled (–10 to –20° C.) solution of the formula 2 peptide and up to about 5 molar equivalents of NMM. After a short time (15 minutes to several hours), the formula 3 peptide is added and the reaction is allowed to proceed for from about 30 minutes to about 10 hours depending on the reactants, the solvent and concentration of reactants. After this initial reaction period the reaction is allowed to warm to room temperature. The product is isolated in any convenient manner such as by washing the reaction mixture with acid, mild base solution such as dilute sodium bicarbonate solution, and brine, and subsequently drying the organic phase and subsequently by evaporation of any solvent. Solvents for this reaction can be any convenient and appropriate solvent such as those mentioned above and preferably will be methylene chloride or a methylene chloride/acetonitrile mixture.

The protecting group is removed from the formula 4 compound in any appropriate manner and the procedure will, of course, depend on the nature of the protecting group and the nature of any other reactive groups on the compound. For example, when the protecting group is a t-butyloxycarbonyl (Boc) group, the formula 4 compound can be converted to the formula 5 compound salt by treatment with gaseous hydrogen chloride in ethyl acetate. When the protecting group is a carbobenzyloxy (Cbz) group, the formula 4 compound can be converted to the formula 5 compound by catalytic hydrogenation.

The formula 2 peptide is prepared by sequentially coupling the requisite amino acids using conventional techniques. In some instances the required di- and tri-peptides are commercially available.

In coupling individual amino acids or peptides, appropriate side chain protecting groups are employed. The selection and use of an appropriate protecting group for these side chain functionalities is within the ability of those skilled in the art and will depend upon the amino acid to be protected and the presence of other protected amino acid residues in the peptide. The selection of such a side chain protecting group is critical in that it must not be removed during the deprotection and coupling steps of the synthesis. For example, when Boc is used as the αamino protecting group, the following side chain protecting groups are suitable: p-toluenesulfonyl (tosyl) moieties can be used to protect the amino side chains of amino acids such as Lys; and a 2-bromocarbobenzoxy (2Br-Z) moiety can be used to protect the hydroxy containing side chains of amino acids such as Tyr. These side chain protecting groups are added and removed according to standard practices and procedures well known in the art. It is preferred to deprotect these side chain protecting groups with a solution of anisole in anhydrous hydrogen fluoride (1:10). Typically, deprotection of side chain protecting groups is performed after the peptide chain synthesis is complete but these groups can alternatively be removed at any other appropriate time. It is preferred to deprotect these side chains at the same time as the peptide is cleaved from the resin when solid phase synthetic methods are employed.

The formula 3 pentafluoroethyl derivative of the $P_1$ amino acid can be prepared as described in European Patent Application Ser. No. 90114250, published Jan. 30, 1991.

The compounds are then isolated and purified by standard techniques. The desired amino acids, derivatives and isomers thereof can be obtained commercially or can be synthesized according to standard practices and procedures well known in the art.

The following specific examples are given to illustrate the preparation of various compounds of this invention although the scope of the invention is not meant to be limited to the compounds exemplified below.

EXAMPLE 1

Preparation of MC-Val-Pro-Val-$CF_2CF_3$
a) Preparation of Boc-Val-Pro-Val-$CF_2CF_3$ To a stirred solution of Boc-Val-Pro-OH (1.10 g, 3.5 mmole) in $CH_2Cl_2$ (20 ml) under argon, cooled to −17° C., was added NMM (0.40 ml, 3.68 mmole). After 5 minutes, 1 equivalent (0.45 ml, 3.5 mmole) of IBCF was added and a light suspension formed several minutes later. After 20 minutes NMM (0.4 ml, 3.68 mmol) was added followed by a suspension of H-Val-$CF_2CF_3$.HCl (0.88 g, 3.50 mol) in $CH_2Cl_2$ (10 ml) plus $CH_3CN$ (10 ml) dropwise (from an addition funnel) over ca. 15 minutes. The reaction was stirred at −14° to −18° C. for 1 hour and then the cooling bath was removed. The reaction was allowed to warm to room temperature (ca. 40 min.) and diluted with $CH_2Cl_2$ (100 ml). The organic phase was washed with 1 N HCl (3×75 ml), satd. $NaHCO_3$ (2×75 ml), and brine (50 ml). Drying ($Na_2SO_4$) and concentration gave a colorless oil which was placed under high vacuum to give the desired product as a white foam (1.59 g, 88%). Elemental analysis; calculated for $C_{22}H_{34}F_5N_3O_5$: % C=51.26, % H=6.65; % N=8.15. Found: % C=50.80, % H=6.57, % N=7.85.

b) Preparation of H-Val-Pro-Val-$CF_2CF_3$.HCl

Into a stirred solution of the product of part (a) (1.52 g, 2.95 mmole) in ethyl acetate (75 ml) cooled in an ice-water bath was bubbled HCl gas for 10 minutes, after which the reaction flask was capped with a septum. TLC after 1 hour indicated the absence of starting material. The reaction mixture was concentrated, the residue dissolved in ethyl acetate and concentrated (2×) to give a white solid which was dried under high vacuum over KOH pellets. Dried weight was 1.35 g. Elemental Analysis; Calcd for $C_{17}H_{26}F_5N_3O_3$.HCl: % C=45.19, H=6.02; % N=9.30. Found: % C=44.84, % H=6.22; % N=8.88. High resolution mass spectrum calcd for $C_{17}H_{27}F_5N_3O_3$ (MH$^+$)=416.1973, found MH$^+$=416.1972, error=−0.2 ppm.

c) Preparation of MC-Val-Pro-Val-$CF_2CF_3$

To a stirred solution of the product of part (b) (1.06 g, 2.35 mmole) in $CH_2Cl_2$ (100 ml) under argon was added 4-morpholinecarbonyl chloride (1.09 ml, 9.38 mmoles) followed by NMM (0.52 ml, 4.69 mmole). After 105 minutes, the reaction mixture was concentrated to ca. 5 ml and loaded onto a column for chromatography. Flash chromatography (6.5× 12 cm silica gel column), eluting with acetone/EtOAc (30:70), gave an oil. A mixture of ethyl ether and hexane was added and concentrated to give a white solid (0.78 g). Elemental Analysis; calcd for $C_{22}H_{33}F_5N_4O_5$: % C=50.00, % H=6.29, % N=10.60. Found: % C=49.88, % H=6.59, % N=10.62.

EXAMPLE 2

Preparation of
N-[4-(4-Morpholinylsulfonyl)benzoyl]-L-valyl-N-[3,3,4,4,4-pentafluoro-1-(1-methylethyl)-2-oxobutyl]-L-prolinamide To a solution of diisopropylethylamine (1.76 g, 13.6 mmol, 2.37 ml) and morpholine (1.98 g, 22.7 mmol, 1.98 ml) in THF (40 ml) was added, dropwise over 0.5 h, a solution of 4-(chlorosulfonyl)benzoic acid (2.50 g, 11.3 mmol) in THF (17 ml). After stirring at room temperature for 18 h the reaction was poured into $H_2O$ (150 ml) and washed with EtOAc. The aqueous layer was acidified (pH 1) with concentrated HCl, and the precipitate collected, washed with cold $H_2O$, and dried under vacuum over $P_2O_5$ to give 2.68 g (87%) of 4-(4-morpholinylsulfonyl)-benzoic acid as an off-white solid.

To a solution of the benzoic acid derivative prepared above (0.240 g, 0.885 mmol) and NMM (0.446 g, 4.43 mmol, 0.489 ml) in $CH_2Cl_2$ (8.9 ml) at −22° C. under $N_2$ was added IBCF (0.121 g, 0.885 mmol, 0.115 ml), and the reaction stirred at −22° C. for 20 min. The HCL.Val-Pro-Val-$C_2F_5$ (0.400 g, 0.885 mmol) was added in several portions, and the reaction was stirred at −22° C. for 0.5 h, followed by 4 h at room temperature. The reaction was diluted with $CH_2Cl_2$ (30 ml) and then washed successively with 10% HCl (2×15 ml), sat. $NaHCO_3$ (2×15 ml), brine (1×15 ml), and dried over $MgSO_4$. Solvent removal under vacuum gave an off-white foam which was purified by flash chromatography (silica gel; 25/75, hexane/EtOAc) to give 0.295 g (50%) of the title compound as a white solid.

EXAMPLE 3

Preparation of
N-[2-(4-morpholinocarbonyl-3-methylbutanoyl]-Val-Pro-Val-$CF_2CF_3$ a) Preparation of methyl 2.-(4-morpholinocarbonyl)acetate To a solution of methylmalonylchloride (10.0 g, 73.2 mmol) in $CH_2Cl_2$ (200 ml) at 0° C. under $N_2$ was added rapidly dropwise a solution of morpholine (16.0 g, 0.183 mmol, 16.0 ml) in $CH_2Cl_2$ (50 ml), and the reaction stirred at room temperature for 4 h. The reaction was filtered, the filtrate diluted with additional $CH_2Cl_2$ (200 ml), and then washed successively with 10% $HC_1$, sat. $NaHCO_3$, brine, and dried over $MgSO_4$. Solvent removal in vacuo gave a yellow oil which was purified by flash chromatography (silica gel, EtOAc) to give 9.70 g (71%) of the title compound, as a pale yellow oil.

b) Preparation of methyl 2-(4-morpholinocarbonyl)-3-methylbutanoate

To a solution of the compound prepared in Example 3a (9.70 g, 51.8 mmol) in THF at 0° C. under $N_2$ was added NaH (1.71 g, 57.0 mmol, 80% dispersion in mineral oil) in three portions. After the initial reaction subsided the reaction was allowed to warm to room temperature, the isopropyl iodide (13.2 g, 77.7 mmol, 7.77 ml) added, and the reaction heated at 60° C. for 8 h followed by 64 h at room temperature. The reaction was diluted with $CH_2Cl_2$ (30 ml) and then washed with $H_2O$, brine, and dried over $MgSO_4$. Solvent removal in vacuo gave a brown oil which was purified by flash chromatography to yield 7.70 g (65%) of the title compound as an orange oil.

c) Preparation of 2-(4-morpholinocarbonyl)-3-methyl-butanoic acid

To a solution of the compound prepared in Example 3b (7.70 g, 33.6 mmol) in MeOH (150 ml) was added LiOH (37 ml), 1M in $H_2O$) and the reaction stirred at room temperature for 24 h. The reaction was acidified with conc. HCl and the solvent removed in vacuo. The residue was triturated with hexane, collected on a fritted funnel, washed with several portions of hexane, and dried in vacuo over $P_2O_5$ to give 5.82 g (81%) of the title compound as a white solid.

d) Preparation of N-[2-(4-morpholinocarbonyl1-3-methylbutanoyl]-Val-Pro-Val-$CF_2CF_3$ To a suspension of the compound prepared in Example 3c (0.304 g, 1.33 mmol) in $CH_2Cl_2$ (8.9 ml) under $N_2$ was added N-methylmoprpholine (0.446 g, 4.43 mmol, 0.489 ml), and the resulting clear, colorless solution cooled to −22° C. The IBCF (0.182 g, 1.33 mmol, 0.173 ml) was added and the reaction stirred for 20 min, followed by addition of the HCl.Val-Pro-Val-$C_2F_5$ in one portion. After stirring at 22° C. for 4 h the reaction was diluted with additional $CH_2C_{12}$ (35 ml) and washed successively with 10% HCl (3×20 ml), sat. $NaHCO_3$ (2×20 ml), brine (1×20 ml), and dried over $MgSO_4$. Solvent removal in vacuo followed by purification by flash chromatography (silica gel; 20/80, acetone/EtOAc) gave 0.343 g (63%) of the title compound as a white foam.

The foregoing describes in detail the generic and specific aspects of the scope of the invention as well as the manner of making and using the invention. In addition thereto, although such procedures are known in the art, references setting forth state of the art procedures by which the compounds may be evaluated for their biochemical effects are also included herein.

By following the techniques referenced above, as well as by utilization of other known techniques, as well as by comparison with compounds known to be useful for treatment of the above-mentioned disease states, it is believed that adequate material is available to enable one of ordinary skill in the art to practice the invention. Of course, in the end-use application of the compounds of this invention, the compounds are preferably formulated into suitable pharmaceutical preparations such as tablets, capsules or elixers, for oral administration or in sterile solutions or suspensions for parenteral administration. The compounds of this invention can be administered to patients (animals and human) in need of such treatment in a dosage range of 5 to 500 mg per patient generally given several times, thus giving a total daily dose of from 5 to 2000 mg per day. As stated above, the dose will vary depending on severity of disease, weight of patient and other factors which a person skilled in the art will recognize.

Typically the compounds described above are formulated into pharmaceutical compositions as discussed below.

About 10 to 500 mg of a compound or mixture of compounds of formula 1 or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may he present as coatings or to otherwise modify the physical form of the dosage unit. For instance, tablets may be coated with shellac, sugar or both. A syrup or elixer may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into The active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound having the formula

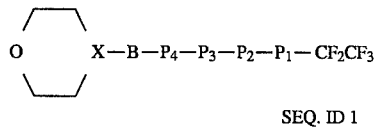

SEQ. ID 1 wherein

B is a group of the formulae

,

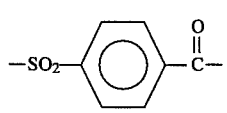

and

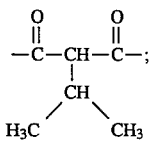;

$P_1$ is Nva or Val;
$P_2$ is Pro;
$P_3$ Ile, Val or Ala;
$P_4$ is Ala or a bond; and
X is N;
or a hydrate or pharmaceutically acceptable salt thereof.

2. A compound of claim 1 selected from MCBz-Ala-Ala-Pro-Val-$C_2F_5$ (SEQ. ID 3) and MCBz-Val-Pro-Val-$C_2F_5$.

3. A compound according to claim 2 wherein the compound is MCBz-Val-Pro-Val-$C_2F_5$.

4. A compound according to claim 1 wherein the compound is N-[4-(4-morpholinylsulfonyl)benzoyl]-L-valyl-N-[3,3,4,4,4-pentafluoro-1-(1-methylethyl)-2 -oxobutyl]-L-prolinamide represented by the formula:

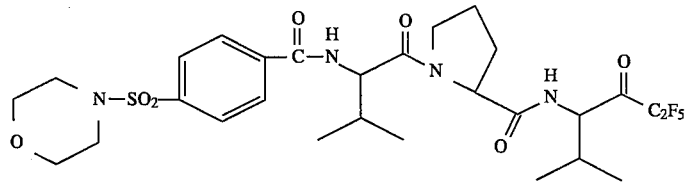

5. A compound according to claim 1 wherein the compound is N-[2-(4-morpholinocarbonyl-3-methylbutanoyl]-Val-Pro-Val-$CF_2CF_3$ represented by the formula:

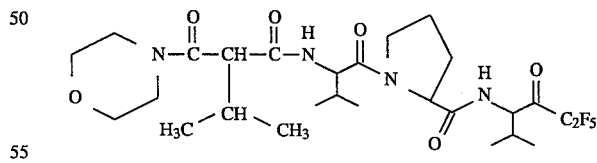

6. A pharmaceutical composition comprising a compound of claim 1 and a pharmaceutically acceptable carrier.

7. A method of treating a patient afflicted with an inflammatory disease, said method comprising the administration to said patient a therapeutically effective amount of a compound of claim 1.

8. A method according to claim 7 wherein said inflammatory disease is emphysema.

* * * * *

UNITED STATES PATENT AND TRADEMARK OFFICE
CERTIFICATE OF CORRECTION

PATENT NO. : 5,478,811
DATED : December 26, 1995
INVENTOR(S) : Norton P. Peet, Michael R. Angelastro, Joseph P. Burkhart

It is certified that error appears in the above-identified patent and that said Letters Patent is hereby corrected as shown below:

Column 1, Line 60 patent reads: "-4-acid" and should read ---4-carboxylic acid--.

Column 2, Line 50 patent reads: "[2.2.21]" and should read--[2.2.2]-.

Column 10, Line 39 patent reads: "αamino" and should read--α-amino-.

Column 11, Line 33 patent reads: "H=" and should read--$^8$H--.

Column 13, Line 2 patent reads: "C$_{12}$" and should read--Cl$_2$--.

Column 13, Line 53 patent reads: "May he" and should read--may be--.

Signed and Sealed this

Eighteenth Day of March, 1997

BRUCE LEHMAN

*Attest:*

*Attesting Officer*         Commissioner of Patents and Trademarks